United States Patent
Benz et al.

(10) Patent No.: US 11,504,420 B2
(45) Date of Patent: Nov. 22, 2022

(54) AGGF1 IMMUNOGENIC COMPOSITIONS

(71) Applicant: NANTOMICS, LLC, Culver City, CA (US)

(72) Inventors: Stephen Charles Benz, Santa Cruz, CA (US); Andrew Nguyen, San Jose, CA (US); Charles Joseph Vaske, Santa Cruz, CA (US); John Zachary Sanborn, Santa Cruz, CA (US)

(73) Assignee: NantOmics, LLC, Culver City, CA (US)

( * ) Notice: Subject to any disclaimer, the term of this patent is extended or adjusted under 35 U.S.C. 154(b) by 481 days.

(21) Appl. No.: 16/571,008

(22) Filed: Sep. 13, 2019

(65) Prior Publication Data
US 2020/0093907 A1   Mar. 26, 2020

Related U.S. Application Data

(63) Continuation of application No. 15/565,203, filed as application No. PCT/US2016/026798 on Apr. 8, 2016.

(60) Provisional application No. 62/144,745, filed on Apr. 8, 2015.

(51) Int. Cl.
| | |
|---|---|
| A61K 39/00 | (2006.01) |
| C12N 5/09 | (2010.01) |
| C07K 16/30 | (2006.01) |
| G01N 33/574 | (2006.01) |
| C07K 16/22 | (2006.01) |
| C07K 14/47 | (2006.01) |
| A61K 47/68 | (2017.01) |
| C12N 5/0783 | (2010.01) |

(52) U.S. Cl.
CPC ............ *A61K 39/001102* (2018.08); *A61K 39/001144* (2018.08); *A61K 47/6851* (2017.08); *C07K 14/4702* (2013.01); *C07K 16/22* (2013.01); *C07K 16/30* (2013.01); *C12N 5/0638* (2013.01); *C12N 5/0646* (2013.01); *C12N 5/0693* (2013.01); *G01N 33/57407* (2013.01); *A61K 2039/505* (2013.01); *A61K 2039/53* (2013.01); *A61K 2039/80* (2018.08); *A61K 2039/812* (2018.08); *A61K 2039/892* (2018.08); *C07K 2317/34* (2013.01); *C07K 2319/55* (2013.01); *C07K 2319/60* (2013.01)

(58) Field of Classification Search
None
See application file for complete search history.

(56) References Cited

U.S. PATENT DOCUMENTS

| | | |
|---|---|---|
| 7,473,532 B2 | 1/2009 | Darfler et al. |
| 8,207,315 B2 | 6/2012 | Wang et al. |
| 8,652,473 B2 | 2/2014 | Johns et al. |
| 2005/0048070 A1 | 3/2005 | Ditzel et al. |
| 2010/0202968 A1 | 8/2010 | Nitsch et al. |
| 2010/0203109 A1 | 8/2010 | Herlyn et al. |
| 2011/0293637 A1 | 12/2011 | Hacohen et al. |
| 2012/0059670 A1 | 3/2012 | Sanborn et al. |
| 2012/0066001 A1 | 3/2012 | Sanborn et al. |
| 2015/0125463 A1 | 5/2015 | Cogswell et al. |
| 2016/0101170 A1 | 4/2016 | Hacohen et al. |
| 2016/0339090 A1 | 11/2016 | Hachen et al. |
| 2017/0032082 A1 | 2/2017 | Nguyen et al. |
| 2018/0141998 A1 | 5/2018 | Nguyen et al. |
| 2019/0099475 A1 | 4/2019 | Benz et al. |

FOREIGN PATENT DOCUMENTS

| | | |
|---|---|---|
| CA | 2 987 730 A1 | 10/2016 |
| CA | 2 988 388 A1 | 10/2016 |
| CN | 108513593 A | 9/2018 |
| CN | 108701173 A | 10/2018 |
| EP | 2279749 A1 | 2/2011 |
| EP | 3 280 738 A1 | 2/2018 |
| EP | 3 286 361 A1 | 2/2018 |
| EP | 3 362 930 A1 | 8/2018 |
| JP | 2018-513187 A | 5/2018 |
| JP | 2018-532736 A | 11/2018 |
| KR | 10-2018-0087244 A | 8/2018 |
| MX | 2017013613 A | 9/2018 |
| WO | 2011/143656 A2 | 11/2011 |
| WO | 2011/143656 A3 | 8/2012 |
| WO | 2014/052707 A2 | 4/2014 |
| WO | 2015/058159 A1 | 4/2015 |
| WO | 2015095811 A2 | 6/2015 |
| WO | 2015103037 A2 | 7/2015 |
| WO | WO 2015/191666 | * 12/2015 |
| WO | 2016/164833 A1 | 10/2016 |
| WO | 2016/172722 A1 | 10/2016 |
| WO | 2017/035392 A1 | 3/2017 |
| WO | 2017/066357 A1 | 4/2017 |

OTHER PUBLICATIONS

Office Action received in Canadian Patent Application Serial No. 2987730 dated Sep. 17, 2019, 4 pages.
Alexandrov et al. "Signatures of mutational processes in human cancer", Nature, 2013, vol. 500, pp. 415-421.
Dung T. Le et al, "PD-1 Blockade in Tumors with Mismatch-Repair Deficiency", The New England Journal of Medicine, - NEJM -, US, (Jun. 25, 2015), vol. 372, No. 26, doi:10.1056/NEJMoa1500596, ISSN 0028-4793, pp. 2509-2520.
E. M. Van Allen et al, "Genomic correlates of response to CTLA-4 blockade in metastatic melanoma", Science, US, (Oct. 9, 2015), vol. 350, No. 6257, ISSN 0036-8075, pp. 207-211.
First Office Action received for Australian Patent Application Serial No. 2016339035, dated Nov. 6, 2019, 04 pages.

(Continued)

*Primary Examiner* — Laura B Goddard
(74) *Attorney, Agent, or Firm* — Martin Fessenmaier; Umberg Zipser LLP

(57) ABSTRACT

Certain universal neoepitopes and cancer specific neoepitopes and methods therefore are presented that may be used in immunotherapy and cancer diagnosis. Preferred therapeutic and diagnostic compositions include antibodies or fragments thereof that bind to neoepitopes on cancer cells.

9 Claims, No Drawings

Specification includes a Sequence Listing.

(56) References Cited

OTHER PUBLICATIONS

Snyder et al., "Genetic basis for clinical response to CTLA-4 blockade in melanoma", New England Journal of Medicine, (2014), vol. 371, No. 23, pp. 2189-2199.
Carter Paul, "Improving The Efficacy of Antibody-Based Cancer Therapies," Nature Reviews, Cancer, Nov. 2001, vol. 1, pp. 118-129.
Fritsch, et al., "HLA-Binding Properties of Tumor Neoepitopes In Humans," Cancer Immunology Research, Jun. 2014, vol. 2, No. 6, pp. 522-529.
International Search Report and Written Opinion received for PCT Application Serial No. PCT/US2016/029244 dated Aug. 9, 2016, 15 pages.
Parmiani et al., "Integrating Immune Checkpoint Blockade with Anti-Neo/Mutated Antigens Reactivity to Increase the Clinical Outcome of Immunotherapy", Vaccines, 2015, vol. 3, pp. 420-428.
Rooij et al., "Tumor Exome Analysis Reveals Neoantigen-Specific T-Cell Reactivity in an Ipilimumab-Responsive Melanoma", Journal of Clinical Oncology, Nov. 10, 2013, vol. 31, No. 32, pp. e439-e442.
Castle et al., "Exploiting the Mutanome for Tumor Vaccination", Cancer Research, Mar. 1, 2012, vol. 72, No. 5, pp. 1081-1091.
Hacohen et al., "Getting Personal with Neoantigen-Based Therapeutic Cancer Vaccines", Cancer Immunology research, Jul. 2013, vol. 1, No. 1, p. 1-8.
Lundegaard et al., "NetMHC-3.0: accurate web accessible predictions of human, mouse and monkey MHC class I affinities for peptides of length 8-11", Nucleic Acids Research, 2008, vol. 36, pp. W509-W512.
Kelderman et al., "Mismatch Repair-Deficient Cancers Are Targets for Anti-PD-1 Therapy", Cancer Cell, Jul. 13, 2015, vol. 28, pp. 11-13.
Charoentong et al., "Bioinformatics for cancer immunology and immunotherapy", Cancer Immunol Immunother, 2012, vol. 61, pp. 1885-1903.
Rizvi et al., "Mutational landscape determines sensitivity to PD-1 blockade in non-small cell lung cancer", Cancer Immunology, Science, Apr. 3, 2015, vol. 348, No. 6230, pp. 124-128.
Segal et al., "Epitope Landscape in Breast and Colorectal Cancer", Cancer Research, Feb. 1, 2008, vol. 68, No. 3, pp. 889-892.
Sykulev et al., "Evidence that a Single Peptide-MHC Complex on a Target Cell Can Elicit a Cytolytic T Cell Response", Immunity, Jun. 1, 1996, vol. 4, No. 6, pp. 565-571.
Kim et al., "HLA Haplotyping from RNA-seq Data Using Hierarchical Read Weighting", PLoS One, Jun. 2013, vol. 8, No. 6, pp. 1-10.
Warren et al., "Derivation of HLA types from shotgun sequence datasets", Genome Medicine, 2012, vol. 4, No. 12, pp. 1-8.
Liu et al., "ATHLATES: accurate typing of human leukocyte antigen through exome sequencing", Nucleic Acids Research, Jun. 8, 2013, vol. 41, No. 14, pp. 1-8.
Bai et al., "Inference of high resolution HLA types using genome-wide RNA or DNA sequencing reads", BMC Genomics, 2014, vol. 15, No. 325, pp. 1-16.
Amalfitano et al., "Production and Characterization of Improved Adenovirus Vectors with the E1, E2b, and E3 Genes Deleted", Journal of Virology, Feb. 1998, vol. 72, No. 2, pp. 926-933.
Vigneron et al., "Database of T cell-defined human tumor antigens: the 2013 update", Cancer Immunity, Jul. 15, 2013, vol. 13, 6 pages.
Carmen et al., "Concepts in antibody phage display", Briefings in Functional Genomics and Proteomics, Jul. 2002, vol. 1, No 2, pp. 189-203.
Hosse et al., "A new generation of protein display scaffolds for molecular recognition", Protein Science, Jan. 2006, vol. 15, No. 1, pp. 14-27.
Zhang et al., "Machine Learning Competition in Immunology—Prediction of HLA class I molecules", J Immunology Methods, 2011, vol. 374, p. 1-9.
First Office Action received for Canadian Patent Application Serial No. 2987730 dated Jul. 31, 2018, 06 pages.
Second Office Action received for Canadian Patent Application Serial No. 2987730 dated Feb. 25, 2019, 04 pages.
Haisma H.J, "Monoclonal antibodies and cancer: Studies on the use of monoclonal antibodies for imaging and therapy of cancer, with a special emphasis on ovarian carcinoma", Dec. 8, 1957, 175 pages.
Gubin et al., Tumor neoantigens: building a framework for, personalized cancer immunotherapy, The Journal of Clinical Investigation, Sep. 2015, vol. 125, No. 9, pp. 3413-3421.
Srivastava P.K, "Neoepitopes of Cancers: Looking Back, Looking Ahead", Cancer Immunology Research, Sep. 1, 2015, vol. 3, No. 9, pp. 969-977.
Monteiro J, "Cancer Immunotherapy Scores Again", Cell, Jan. 15, 2015, vol. 160, p. 7-9.
Hundal et al., "pVAC-Seq: A genome-guided in silico approach to identifying tumor neoantigens", Genome Medicine, Jan. 29, 2016, vol. 8, No. 11, p. 1-11.
Akkawi et al., "The human VG5Q gene 2 transcript is over-expressed in colorectal and bladder carcinomas", Gene Therapy Molecular Biology, 2006, vol. 10, pp. 173-178.
Wang et al., "Overexpression of AGGFI 2 is correlated with angiogenesis and poor prognosis of hepatocellular carcinoma", Med. Oncol, 2015,, vol. 32, No. 131, pp. 1-9.
Supplementary European Search report received for European Patent Application Serial No. 16777432 dated Aug. 29, 2018, 03 pages.
Rabizadeh et al., "Comprehensive genomic transcriptomic tumor-normal gene panel analysis for enhanced precision in patients with lung cancer", Oncotarget, Apr. 2018, vol. 9, No. 27, pp. 19223-19232.
Carreno et al., "Supplementary Materials for A dendritic cell vaccine increases the breadth and diversity of melanoma neoantigen-specific T cells", Science, May 15, 2015, vol. 348, No. 6236, pp. 34 pages.
Matsushita et al., "Cancer exome analysis reveals a T-cell-dependent mechanism of cancer immunoediting", Nature, Feb. 16, 2012, vol. 482, 7 pages.
Reuschenbach et al., "A multiplex method for the detection of serum antibodies against in silica-predicted tumor antigens", Cancer Immunol Immunother, Aug. 2014, vol. 63, pp. 1251-1259.
Extended European Search report received for European Patent Application Serial No. 16784102.2 dated Apr. 5, 2019, 13 pages.
Liosa et al., "The vigorous immune microenvironment of microsatellite instable colon cancer is balanced by multiple counter-inhibitory checkpoints", Cancer Discovery, Jan. 2015, vol. 5, pp. 43-51.
First Office Action received for Japanese Patent Application Serial No. 2018519039 dated Nov. 12, 2019, 08 pages (Including English Translation).
International Preliminary Report on Patentability received for PCT Application Serial No. PCT/US2016026798 dated Oct. 10, 2017, 01 pages.
Herbst et al., "Predictive correlates of response to the anti-PD-L1 antibody MPDL3280A in cancer patients", Nature, Nov. 27, 2014, vol. 515, pp. 1-18.
First Office Action received for Russian Patent Application Serial No. 2017145136/10(077299) dated Sep. 13, 2019, 14 pages (Including English Translation).
Non-Final Office Action received for U.S. Appl. No. 15/292,021 dated Dec. 27, 2016, 22 pages.
Final Office Action received for U.S. Appl. No. 15/292,021 dated Jul. 14, 2017, 27 pages.
Non-Final Office Action received for U.S. Appl. No. 15/292,021 dated Dec. 4, 2017, 21 pages.
Final Office Action received for U.S. Appl. No. 15/292,021 dated Jun. 8, 2018, 20 pages.
Non-Final Office Action received for U.S. Appl. No. 15/292,021 dated Oct. 1, 2018, 18 pages.
Final Office Action received for U.S. Appl. No. 15/292,021 dated Mar. 29, 2019, 10 pages.
Extended European Search report received for European Patent Application Serial No. 16777432.2 dated Nov. 30, 2018, 11 pages.
Non-Final office Action Received for U.S. Appl. No. 15/565,203, dated Jun. 18, 2019, 17 pages.

(56) References Cited

OTHER PUBLICATIONS

International Preliminary Report on Patentability Chapter II received for PCT Application Serial No. PCT/US2016/029244 dated Aug. 22, 2017, 18 pages.
Carreno et al., "A dendritic cell vaccine increases the breadth and diversity of melanoma neoantigen-specific T cells". Science, 2018, vol. 348, No. 6236, pp. 8 pages.
International Search Report and Written Opinion received for PCT Application Serial No. PCT/US2016/056692 dated Jan. 11, 2017, 13 pages.
First Examination report received for Australian Patent Application Serial No. 2016253145, dated Jan. 17, 2020, 05 pages.
Communication Pursuant to rule 164(1) EPC received in European Patent Application Serial No. 16784102.2, dated Jan. 3, 2019, 15 pages.
International Preliminary Report received for PCT Application Serial No. PCT/US2016/056692 dated Jan. 9, 2018, 15 pages.
Boegel et al., "HLA typing from RNA-Seq sequence reads", Genome Medicine, 2012, vol. 4, No. 102, 12 pages.
Communication Pursuant to Rule 164(1) EPC received for European Patent Application No. 16777432 dated Aug. 29, 2018, 12 pages.
Summons to attend oral proceedings pursuant to Rule 115(1) EPC received for European Patent Application Serial No. 16777432 dated Aug. 23, 2019, 5 pages.
Fritsch, et al., "Personal neoantigen cancer vaccines," OncoImmunology, vol. 3, Article No. e29311, Internal pp. 1-3 (Jun. 2014).
ISA/KR, International Search Report and Written Opinion, completed Jul. 18, 2016 for PCT Application No. PCT/US2016/026798, 14 pages.
Lutz, et al., "Can we predict mutant neoepitopes in human cancers for patient-specific vaccine therapy?" Cancer Immunology Research, vol. 2, No. 6, pp. 518-521 (Jun. 2014).
Tian et al (Nature, 2004, 427, 640-645).
Wang et al (Med Oneal. 2015,32:131, online publication Mar. 22, 2015).

* cited by examiner

AGGF1 IMMUNOGENIC COMPOSITIONS

CANCER NEOEPITOPES

This application is a continuation application of our copending US application with the Ser. No. 15/565,203, which was filed Oct. 9, 2017, which is a 371 application of our International application with the serial number PCT/US2016/026798, which claims priority to the U.S. provisional application Ser. No. 62/144,745, filed Apr. 8, 2015, and which is incorporated by reference herein.

FIELD OF THE INVENTION

The field of the invention is methods and compositions for cancer neoepitopes, especially as it relates to neoepitopes common to certain cancers.

BACKGROUND

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Random mutations in tumor cells can give rise to unique tumor specific antigens (i.e., cancer neoepitopes or neoepitopes). As such, and at least conceptually, neoepitopes may thus provide a unique precision target for immunotherapy. Additionally, it has been shown that cytolytic T-cell responses can be triggered by very small quantities of peptides (e.g., Sykulev et al., *Immunity*, Volume 4, Issue 6, p565-571, 1 June 1996). In view of these findings, the identification of cancer neoepitopes as therapeutic targets has attracted much attention. Unfortunately, current data tend to support the notion that all or almost all cancer neoepitopes are unique to a patient and specific tumor and therefore fail to provide any useful guidance for development of an immunotherapeutic agent suitable for more than one patient and tumor type (see e.g., Fritsch et al. *Cancer Immunol Res;* 2(6); 1-8). Moreover, as a proper immune reaction is also at least to some degree dependent on a patient's HLA type, development of a 'broad spectrum' immunotherapeutic targeting single neoepitopes has been deemed unlikely as two factors with high variability (neoepitope sequence and HLA-type) must be met.

Thus, even though neoepitopes in tumors can be predicted relatively easily, there is still a need to provide improved compositions and methods for cancer epitopes and their use in the diagnosis and treatment of neoplastic diseases.

SUMMARY OF THE INVENTION

The inventive subject matter is directed to various compositions and methods related to cancer neoepitopes that occur across a variety of different cancers or different subtypes of cancers. In at least some aspects, such cancer neoepitopes also bind to various distinct HLA types and as such may be used as cancer immunotherapeutic agents for multiple and distinct patients. Therefore, and viewed form a different perspective, the inventors discovered various conserved neoepitopes that have a sequence and that occur at a frequency that allows for manufacture of immunotherapeutic compositions for the diagnosis or treatment of cancer or specific cancer types in a significant subpopulation of patients expressing such neoepitopes.

In one aspect of the inventive subject matter, the inventors contemplate a method of directing an agent to a cancer cell that includes a step of contacting the cancer cell (preferably in vivo) with an antibody or antibody fragment that binds to a cancer neoepitope in an AGGF1 (angiogenic factor with g-patch and FHA domains 1) protein, wherein the cancer neoepitope is formed by a V202L mutation in the AGGF1 protein. In such contemplated methods the cancer cell may be a BRCA (breast cancer) cell, a CESC (cervical squamous cell carcinoma) cell, a HNSC (head and neck squamous cell carcinoma) cell, a LIHC (liver hepatocellular carcinoma) cell, a LUAD (lung adenocarcinoma) cell, a LUSC (lung squamous cell carcinoma) cell, an OV (ovarian cancer) cell, a READ (renal adenocarcinoma) cell, a STAD (stomach adenocarcinoma) cell, a THCA (thyroid carcinoma) cell, or a UCEC (uterine corpus endometrioid carcinoma) cell.

Moreover, it is contemplated that the antibody or antibody fragment may be synthetic or may comprise an IgG or other type of antibody, a Fab, a $F(ab')_2$, or a scFv, each of which may or may not be further coupled to a therapeutic agent, a radiologic agent, or an imaging agent. Where desired, the antibody or fragment thereof may also be coupled to a portion of a T-cell receptor, and/or may be coupled to a cytotoxic T-cell or an NK cell. Depending on the type of antibody, it is contemplated that the antibody or fragment thereof may be produced in a process that includes a step of immunizing a mammal with a peptide having SEQ ID NO:1, SEQ ID NO:2, or SEQ ID NO:3. Therefore, it should be noted that the cancer neoepitope may have a sequence of SEQ ID NO:1, SEQ ID NO:2, or SEQ ID NO:3.

Therefore, the inventors also contemplate the use of an antibody or fragment thereof to direct a diagnostic or therapeutic agent to a cancer cell, wherein the antibody or fragment thereof binds to a cancer neoepitope in an AGGF1 protein, and wherein the cancer neoepitope is formed by a V202L mutation in the AGGF1 protein. Most typically, the cancer cell will be selected form the group consisting of a BRCA (breast cancer) cell, a CESC (cervical squamous cell carcinoma) cell, a HNSC (head and neck squamous cell carcinoma) cell, a LIHC (liver hepatocellular carcinoma) cell, a LUAD (lung adenocarcinoma) cell, a LUSC (lung squamous cell carcinoma) cell, an OV (ovarian cancer) cell, a READ (renal adenocarcinoma) cell, a STAD (stomach adenocarcinoma) cell, a THCA (thyroid carcinoma) cell, and a UCEC (uterine corpus endometrioid carcinoma) cell. As noted before, it is contemplated that the diagnostic or therapeutic agent may comprise a radiologic agent, an imaging agent, a portion of a T-cell receptor, a cytotoxic T-cell, an NK cell, or that the therapeutic agent is the antibody.

Viewed form a different perspective, the inventors also contemplate an antibody or fragment thereof that binds to a cancer neoepitope in an AGGF1 protein, wherein the cancer neoepitope is formed by a V202L mutation in the AGGF1 protein, and wherein the cancer neoepitope has a sequence of SEQ ID NO:1, SEQ ID NO:2, or SEQ ID NO:3. In at least some aspects, the antibody may be an IgG antibody or may further comprise a portion of a T-cell receptor, or may be configured as a scFv. As before, it is contemplated that the antibody or fragment thereof may further comprise a therapeutic or diagnostic agent.

Consequently, the inventors also contemplate an immunologic composition that includes a carrier to which a peptide is coupled that has a sequence of SEQ ID NO:1, SEQ ID NO:2, or SEQ ID NO:3, wherein the composition is formulated as a vaccine. Where desired, the peptide may also be further coupled to at least one additional cancer neoepitope peptide.

In other aspects of the inventive subject matter, the inventors also contemplate a recombinant nucleic acid that includes a promoter operably coupled to a sequence encoding a protein having a sequence of SEQ ID NO:1, SEQ ID NO:2, or SEQ ID NO:3. For example, especially preferred recombinant nucleic acids include viral or bacterial expression vectors. Where desired, the recombinant nucleic acid may further comprise at least one additional sequence that encodes at least one additional cancer neoepitope peptide.

In still further aspects of the inventive subject matter, the inventors also contemplate a method of directing an agent to a breast cancer cell that includes a step of contacting (e.g., in vivo) the cancer cell with an antibody or fragment thereof that binds to a cancer neoepitope having a sequence of any one of SEQ ID NO:4 to SEQ ID NO:28, of any one of SEQ ID NO:29 to SEQ ID NO:53, of any one of SEQ ID NO:54 to SEQ ID NO:78, or of any one of SEQ ID NO:79 to SEQ ID NO:103.

For example, where the cancer cell is a triple negative breast cancer cell, the neoepitope may have a sequence of any one of SEQ ID NO:4 to SEQ ID NO:28, or where the cancer cell is a ER (estrogen receptor) positive breast cancer cell, the neoepitope may have a sequence of any one of SEQ ID NO:29 to SEQ ID NO:53, or where the cancer cell is a PR (progesterone receptor) positive breast cancer cell, the neoepitope may have a sequence of any one of SEQ ID NO:54 to SEQ ID NO:78, or where the cancer cell is a HER2 (human epidermal growth factor receptor 2) positive breast cancer cell, and wherein the neoepitope has a sequence of any one of SEQ ID NO:79 to SEQ ID NO:103.

While not limiting the inventive subject matter, it is contemplated that the antibody or fragment thereof may comprise an IgG antibody, a Fab, a F(ab')2, and a scFv, and/or that the antibody or fragment thereof may further comprise a therapeutic agent, an imaging agent, or a radiologic agent. In other examples, the antibody or fragment thereof may also be coupled to a portion of a T-cell receptor, or may be coupled to a cytotoxic T-cell or an NK cell. It should also be appreciated that the antibody or fragment thereof may be produced in a process that includes a step of immunizing a mammal with any one of a peptide having SEQ ID NO:4 to SEQ ID NO:103.

Consequently, the inventors also contemplate the use an antibody or fragment thereof to direct a diagnostic or therapeutic agent to a cancer cell, wherein the antibody or fragment thereof binds to a cancer neoepitope having a sequence of any one of SEQ ID NO:4 to SEQ ID NO:28, of any one of SEQ ID NO:29 to SEQ ID NO:53, of any one of SEQ ID NO:54 to SEQ ID NO:78, or of any one of SEQ ID NO:79 to SEQ ID NO:103. In preferred uses, the cancer cell is a triple negative breast cancer cell, and the neoepitope has a sequence of any one of SEQ ID NO:4 to SEQ ID NO:28, or the cancer cell is a ER (estrogen receptor) positive breast cancer cell, and the neoepitope has a sequence of any one of SEQ ID NO:29 to SEQ ID NO:53, or the cancer cell is a PR (progesterone receptor) positive breast cancer cell, and the neoepitope has a sequence of any one of SEQ ID NO:54 to SEQ ID NO:78, or the cancer cell is a HER2 (human epidermal growth factor receptor 2) positive breast cancer cell, and the neoepitope has a sequence of any one of SEQ ID NO:79 to SEQ ID NO:103. In further preferred uses, the diagnostic or therapeutic agent may comprise a radiologic agent, an imaging agent, a portion of a T-cell receptor, a cytotoxic T-cell, or an NK cell, or therapeutic agent may be the antibody (e.g., in form of an IgG).

Viewed from another perspective, the inventors therefore also contemplate an antibody or fragment thereof that binds to a cancer neoepitope having a sequence of any one of SEQ ID NO:4 to SEQ ID NO:28, of any one of SEQ ID NO:29 to SEQ ID NO:53, of any one of SEQ ID NO:54 to SEQ ID NO:78, or of any one of SEQ ID NO:79 to SEQ ID NO:103. Such antibodies or fragments may be an IgG or may further comprises a portion of a T-cell receptor, or may be configured as a scFv, and/or may further comprise a therapeutic or diagnostic agent.

In still further aspects of the inventive subject matter, the inventors also contemplate an immunologic composition that includes a carrier to which is coupled a peptide having a sequence of any one of SEQ ID NO:4 to SEQ ID NO:28, of any one of SEQ ID NO:29 to SEQ ID NO:53, of any one of SEQ ID NO:54 to SEQ ID NO:78, or of any one of SEQ ID NO:79 to SEQ ID NO:103, wherein the composition is formulated as a vaccine. Where desired, the peptide may be further coupled to at least one additional cancer neoepitope peptide.

On the other hand, the inventors also contemplate a recombinant nucleic acid that comprises a promoter operably coupled to a sequence that encodes a protein having a sequence of any one of SEQ ID NO:4 to SEQ ID NO:28, of any one of SEQ ID NO:29 to SEQ ID NO:53, of any one of SEQ ID NO:54 to SEQ ID NO:78, or of any one of SEQ ID NO:79 to SEQ ID NO:103. Most preferably, the recombinant nucleic acid is a viral expression vector, and/or may further comprises at least one additional sequence that encodes at least one additional cancer neoepitope peptide.

Various objects, features, aspects and advantages of the inventive subject matter will become more apparent from the following detailed description of preferred embodiments.

DETAILED DESCRIPTION

The inventors have discovered neoepitopes that are common among a subpopulation of cancer patients diagnosed with a relatively wide spectrum of cancers (e.g., breast cancer, cervical squamous cell carcinoma, head and neck squamous cell carcinoma, lung squamous cell carcinoma, liver hepatocellular carcinoma, lung adenocarcinoma, ovarian cancer, renal adenocarcinoma, stomach adenocarcinoma, thyroid carcinoma, uterine corpus endometrioid carcinoma, etc.), or subpopulation of a group of cancer types (e.g., triple negative breast cancer, ER positive breast cancer cell, PR positive breast cancer, HER2 positive breast cancer).

More specifically, and with respect to discovery of neoepitopes contemplated and/or presented herein, preferred methods will include a step of performing an omics analysis. Most typically, the omics analysis will be at least a whole genome sequencing, or an exome sequencing of the patient's genome, preferably in conjunction with a matched normal (non-diseased) sample of the same patient. There are numerous such methods known in the art, and specific suitable examples for omics analysis are described in US20120059670A1 and US20120066001A1, which are incorporated by reference herein. It should therefore be appreciated that not only cancer specific mutations can be readily detected, but that such information is also specific to a particular patient. Additionally, it is generally preferred that the omics analysis also includes an analysis of gene expression (transcriptomic analysis) to so help identify the level of expression for the gene with a mutation. Viewed from another perspective, transcriptomic analysis may be suitable, alone or in combination with genomic analysis, to identify and quantify genes having a cancer and patient specific mutation. There are numerous methods of transcriptomic analysis known in the art, and all of the known methods are deemed suitable for use herein. For example, and among other choices, quantitative PCR or hybridization techniques and in silico determination of relative frequency are contemplated. Taken the above into consideration, it should therefore be appreciated that a patient sample comprising DNA and RNA from tumor and matched normal tissue can be used to identify specific mutations and to quantify such mutations.

Of course, it should also be appreciated that further downstream analysis may be performed on the so identified sequence differences to identify those that lead to a new peptide sequence based on the cancer and patient specific mutation. In other words, silent mutations may be eliminated from the list of identified neoepitopes. Neoepitopes may therefore be identified by considering the type (e.g., deletion, insertion, transversion, transition, translocation) and impact of the mutation (e.g., non-sense, missense, frame shift, etc.), and may as such serve as a first content filter through which silent and other non-relevant (e.g., non-expressed) mutations are eliminated. It should further be appreciated that neoepitope sequences can be defined as sequence stretches with relatively short length (e.g., 7-11 mers) wherein such stretches will include the change(s) in the amino acid sequences. Most typically, the changed amino acid will be at or near the central amino acid position. For example, a typical neoepitope may have the structure of $A_4$-N-$A_4$, or $A_3$-N-$A_5$, or $A_2$-N-$A_7$, or $A_5$-N-$A_3$, or $A_7$-N-$A_2$, where A is an amino acid and N is a changed amino acid (relative to wild type or matched normal)

The so obtained neoepitopes may then be subject to further detailed analysis and filtering using predefined structural and expression parameters, and/or sub-cellular location parameters. For example, it should be appreciated that neoepitope sequences are only retained provided they will meet a predefined expression threshold (e.g., at least 20%, 30%, 40%, 50%, or higher expression of matched normal or average/reference value for healthy tissue) and/or are identified as having a membrane associated location (e.g., are located at the outside of a cell membrane of a cell). Further contemplated analyses may include structural calculations that delineate whether or not a neoepitope is likely to be solvent exposed, presents a structurally stable epitope, etc.

In yet another aspect of filtering, the neoepitopes may be compared against a database that contains known human sequences to so avoid use of a human-identical sequence. Moreover, filtering may also include removal of neoepitope sequences that are due to SNPs in the patient. For example, The Single Nucleotide Polymorphism Database (dbSNP) is a free public archive for genetic variation within and across different species developed and hosted by the National Center for Biotechnology Information (NCBI) in collaboration with the National Human Genome Research Institute (NHGRI). Although the name of the database implies a collection of one class of polymorphisms only (i.e., single nucleotide polymorphisms (SNPs)), it in fact contains a relatively wide range of molecular variation: (1) SNPs, (2) short deletion and insertion polymorphisms (indels/DIPs), (3) microsatellite markers or short tandem repeats (STRs), (4) multinucleotide polymorphisms (MNPs), (5) heterozygous sequences, and (6) named variants. The dbSNP accepts apparently neutral polymorphisms, polymorphisms corresponding to known phenotypes, and regions of no variation. Using such database, the patient and tumor specific neoepitopes may be further filtered to remove those know sequences, yielding a therapeutic sequence set with a plurality of neoepitope sequences.

As preferred neoepitopes will be employed in immunotherapy, the neoepitopes are at least in some aspects of the inventive subject matter further filtered by their ability to bind to an HLA type, and most typically to an HLA type of one or more patients. Thus, contemplated methods and compositions will include HLA binding prediction or the use of HLA-matched neoepitopes. There are numerous manners of determining a person's HLA type, and all manners including conventional laboratory methods (e.g., sequence-specific oligonucleotide probe hybridization, PCR amplification with sequence-specific primers, Sanger sequencing, or sero-typing . . . ) and in silico methods (e.g., from RNA reads as described in *Genome Med.* 2013, 4 (12): 102- or *PLoS One.* 2013, 8 (6): e67885-, or from DNA reads as described in *Genome Med.* 2012, 4 (12): 95- or *Nucleic Acids Res.* 2013, 41 (14): e142-, or *BMC Genomics* 2014, 15:325) are deemed suitable for use herein. Most typically, HLA binding is considered strong for (calculated) Kd values of <50 nM, while binding is considered moderate for (calculated) Kd values of <500 nM.

Therefore, neoepitopes can be scored/ranked based on allele frequency multiplied by the transcripts per million number to get a likelihood score. This score can then be further augmented using HLA information and calculated or actual binding affinity to the patient's HLA type. For example, an exemplary ranking format may be:

>254 NM_001000.3 RPL39 Missense p.M29K A->T Normal: WIRMKTGNK, AF: 0.179104477612 TPM: 1023.96 TPM_MEDIAN: 7.35 LL: 183.395820896 netMHC: 242.96 Allele: HLA-A0301 WIRKKTGNK.

Here, the file is a FASTA formatted file, and entries start with the '>' character, which just reports sample information. The next line is the neoepitope. In the sample information line contains a number used for indexing the sample (e.g., 254), the Refseq Gene ID (e.g., NM_001000.3), the HUGO common name (e.g., RPL39), the variant classification (e.g., Missense), the protein change (e.g., p.M29K), the base pair change (e.g., A->T), the normal epitope (e.g., Normal: WIRMKTGNK), allele frequency (e.g., AF: 0.179104477612), Transcripts per million for this gene (e.g., TPM: 1023.96), TPM_MEDIAN which is the median expression level of all the genes (e.g., TPM_MEDIAN: 7.35), the LL score which is just AF×TPM (e.g., LL: 183.395820896), the netMHC predicted binding value (e.g., netMHC: 242.96), and the specific HLA allele that the neoepitope binds to (e.g., Allele: HLA-A0301). The next line is then the neoepitope (e.g., WIRKKTGNK).

Therefore, neoepitopes suitable for use herein may be identified in a process that uses incremental synchronous alignment of tumor and matched normal BAM (or SAM or GAR) files to so identify differences genuine to the tumor and specific to the patient. Most typically the differences are recorded in VCF format and identified neoepitopes are further processed as discussed above to select for (highly, at least 50% of normal) expressed neoepitopes that bind with an at least moderate, and more preferably strong affinity to the patient's HLA type. Of course, it should be appreciated that the so obtained list of filtered neoepitopes is further compared to known epitopes (of the same patient) to avoid to selection of naturally occurring sequences.

Notably, and as further described in more detail below, the inventors conducted large scale analyses of known tumor and matched normal sequences in omics databases and were able to identify several neoepitopes that occurred in a subpopulation of patients diagnosed with various cancers, and that occurred in cancer sub-types of patients diagnosed with breast cancer.

EXAMPLES

Based on the ever increasing number in available omics data, the inventors queried publicly available databases whether or not universal cancer neoepitopes could exist. To that end, the inventors reviewed the TCGA data sets in an effort to identify recurrent neoepitopes in cancers, and to so potentially provide an avenue to universal or cancer specific immune therapeutic agents. Table 1 below lists TCGA data sets (whole genome sequencing), with the relevant cancer subtypes and epitope information found within these data sets.

TABLE 1

| Cancer | Samples | Total Epitope | Unique Epitope/Sample | Total Epitope/Sample | Average Coding Variant Count | Highest Repeat Epitope Across Samples | Max Recurrent/ Total Sample |
|---|---|---|---|---|---|---|---|
| BLCA | 23 | 35781 | 1555 | 1583 | 180 | 4 | 0.17 |
| BRCA | 98 | 69791 | 712 | 736 | 86 | 12 | 0.12 |
| CESC | 16 | 11662 | 728 | 763 | 86 | 2 | 0.13 |
| COAD | 46 | 334807 | 7321 | 7538 | 816 | 9 | 0.20 |
| DLBC | 7 | 7491 | 1070 | 1110 | 125 | 4 | 0.57 |
| GBM | 27 | 8551 | 316 | 334 | 50 | 3 | 0.11 |
| HNSC | 50 | 57154 | 1143 | 1179 | 135 | 9 | 0.18 |
| KICH | 49 | 13994 | 285 | 317 | 36 | 4 | 0.08 |
| KIRC | 40 | 20892 | 522 | 548 | 59 | 4 | 0.10 |
| KIRP | 14 | 8540 | 610 | 652 | 68 | 2 | 0.14 |
| LAML | 4 | 112 | 28 | 39 | 21 | 1 | 0.25 |
| LGG | 13 | 2803 | 215 | 230 | 24 | 10 | 0.77 |
| LIHC | 46 | 33794 | 734 | 774 | 89 | 4 | 0.09 |
| LUAD | 45 | 75651 | 1681 | 1716 | 193 | 6 | 0.13 |
| LUSC | 39 | 87087 | 2233 | 2285 | 262 | 5 | 0.13 |
| OV | 48 | 27551 | 573 | 639 | 72 | 7 | 0.15 |
| PRAD | 20 | 3031 | 151 | 212 | 22 | 2 | 0.10 |
| READ | 16 | 105482 | 6592 | 6592 | 6679 | 4 | 0.25 |
| SARC | 17 | 7686 | 452 | 474 | 54 | 1 | 0.06 |
| SKCM | 39 | 175792 | 4507 | 4583 | 535 | 11 | 0.28 |
| STAD | 29 | 112816 | 3890 | 4086 | 387 | 5 | 0.17 |
| THCA | 45 | 6266 | 139 | 164 | 19 | 9 | 0.20 |
| UCEC | 44 | 199995 | 4545 | 4690 | 503 | 8 | 0.18 |
| Average | 33.69 | 61162.13 | 1739.21 | 1793.21 | 456.56 | 5.47 | 0.16 |

Notably, the number of epitopes per tumor sample was relatively high, ranging from about 160 (for THCA) to about 6,500 (for READ). Even more notable was the fact that almost all of the epitopes found in a sample were unique epitopes, which at least at first glance seemed to contradict the possibility of shared or common cancer neoepitopes within a cancer type or among two or more cancer types. Interestingly, the fraction of coding variants produced by the neoepitopes was relatively low (at approximately 10% of total neoepitopes), but across all tumor types shared or common cancer neoepitopes nevertheless existed. For example, a single recurrent mutation was shared among about 17% of patients within a cancer subtype (BLCA data set has a single missense mutation in FGFR3 that is present in 4 out of 23 patients).

When considering common or shared neoepitopes across cancers in the TCGA data set, the inventors noted that the highest single recurrent mutation was shared between 3% of all patients as is shown in Table 2 below, which is unexpectedly high when considering the nature of different cancer types and difference in patients.

TABLE 2

| Cancer | Samples | Total Epitope | Unique Epitope/Sample | Total Epitope/Sample | Average Coding Variant Count | Highest Repeat Epitope Across Samples | Repeated/ Total Sample |
|---|---|---|---|---|---|---|---|
| All Cancer | 775 | 1408729 | 1817 | 1878 | 208 | 27 | 0.03 |

Indeed, for the TCGA data set examined, three epitopes were detected in 26 patients out of a total of 775 patients with different cancers (as listed in Table 1). More particularly, these neoepitopes were seen in BRCA, CESC, HNSC, LIHC, LUAD, LUSC, OV, READ, STAD, THCA and UCEC, with ~25% of samples being ovarian serous cystadenocarcinoma. Table 3 below provides more information about this shared cancer neoepitope.

TABLE 3

| 9-Mer | Occurrences in TCGA WGS data set | Gene | Protein Change | Variant Classification |
|---|---|---|---|---|
| AEAALSQTG [SEQ ID NO: 1] | 26 | AGGF1 | p.V202L | Missense |
| ALSQTGFSY [SEQ ID NO: 2] | 26 | AGGF1 | p.V202L | Missense |
| EAALSQTGF [SEQ ID NO: 3] | 26 | AGGF1 | p.V202L | Missense |

As can be readily seen from Table 3, the neoepitope occurred in the same gene and had the same protein change: At position 202 a valine was replaced by a leucine, each time in the same gene AGGF1 (angiogenic factor G patch with FHA domains 1). The AGGF1 is known to encode VG5Q, (vasculogenesis gene on 5q), which promotes angiogenesis and is overexpressed in lung cancers by microarray.

It should be appreciated that according to the American Cancer Society ~1,658,370 new cancer diagnoses are expected for the year 2015. Given that the above neoepitopes will occur in about 3% of all cancers, it must be recognized that about 49,757 patients potentially carry the AGGF1 neoepitope. This prompted the inventors to investigate whether or not the above neoepitopes would have binding affinity to various relatively common HLA types, and computational analyses were performed for selected MHC-I alleles. The results are shown in Table 4 below. Notable, the neoepitope showed strong (<50 nM) calculated binding to five MHC-I alleles, and moderate (<500 nM) binding to five additional MHC-I alleles.

TABLE 4

| Mer | HLA-A*29:02 | HLA-A*30:02 | HLA-B*15:01 | HLA-B*15:02 | HLA-B*15:03 | HLA-B*15:17 | HLA-B*35:01 | HLA-B*40:02 | HLA-B*44:02 | HLA-B*45:01 |
|---|---|---|---|---|---|---|---|---|---|---|
| ALSQTGFSY [SEQ ID NO: 2] | 19 | 29 | 25 | 161 | 59 | 150 | | | | |
| EAALSQTGF [SEQ ID NO: 3] | | | | | | | 432 | 329 | | |
| AEAALSQTG [SEQ ID NO: 1] | | | | | | | | 399 | 67 | 36 |

When considering HLA frequency for specific HLA types over the entire population, the inventors discovered that HLAs that bind to the AGGF1 neoepitopes occur in significant fractions of the US population as shown in Table 5 below (EUR: European ethnicity; AFA: African American ethnicity; API: Asia-Pacific ethnicity; HIS: Hispanic ethnicity).

TABLE 5

| | EUR Frequency | EUR Rank | AFA Freq | AFA Rank | API Freq | API Rank | HIS Freq | HIS Rank |
|---|---|---|---|---|---|---|---|---|
| HLA-A*29:02, | 0.03279 | 6 | 0.03640 | 12 | 0.00141 | 30 | 0.04167 | 8 |
| HLA-A*30:02, | 0.00921 | 15 | 0.06219 | 6 | 0.00056 | 40 | 0.02811 | 12 |
| HLA-B*15:01, | 0.06654 | 4 | 0.00975 | 23 | 0.03480 | 11 | 0.02876 | 10 |
| HLA-B*15:02, | 0.00000 | NA | 0.00083 | 55 | 0.03565 | 10 | 0.00025 | 99 |
| HLA-B*15:03, | 0.00089 | 39 | 0.06245 | 4 | 0.00028 | 88 | 0.01601 | 20 |
| HLA-B*15:17, | 0.00273 | 34 | 0.00602 | 32 | 0.00453 | 40 | 0.00650 | 38 |
| HLA-B*35:01, | 0.05713 | 5 | 0.06494 | 3 | 0.04273 | 5 | 0.06353 | 1 |
| HLA-B*40:02, | 0.00991 | 20 | 0.00353 | 39 | 0.03056 | 14 | 0.04852 | 5 |
| HLA-B*44:02, | 0.09011 | 3 | 0.02116 | 17 | 0.00764 | 32 | 0.03327 | 9 |
| HLA-B*45:01, | 0.00426 | 28 | 0.04502 | 7 | 0.00226 | 52 | 0.01526 | 22 |
| HLA-A Sum | | 0.04200 | | 0.09859 | | 0.00197 | | 0.06978 |
| HLA-B Sum | | 0.23157 | | 0.21370 | | 0.15845 | | 0.21210 |

Based on the above calculations, it can therefore be expected that the AGGF1 cancer neoepitope will be present in about 49,757 patients and will be bound by an HLA type listed above in about 12,000 patients. Viewed form a different perspective, the AGGF1 cancer neoepitope may be effectively presented to a patient's immune system and with be at least potentially accessible as cancer specific target to a significant proportion of patients. Thus, the inventors also contemplate various compositions and methods that make use of the so presented cancer neoepitopes as further discussed in more detail below Encouraged by these results, the inventors also investigated whether or not distinct cancer subtypes would express and/or present cancer neoepitopes specific to the cancer subtype. For example, when looking at the breast cancer results, the inventors stratified the BRCA patient data sets into four distinct subsets following clinically relevant classifications: ER+ (estrogen receptor positive), PR+ (progesterone receptor positive), HER2+ (human epidermal growth factor receptor 2 positive), and triple negative (lacking ER, PR, and HER2) breast cancer.

Notably, Table 6 below shows exemplary results for common neoepitopes in triple negative breast cancer identified from a total of 35 samples. Here the frequency is shown as Repeat, the neoepitope sequence as mer (9-mer), while the affected gene is indicated along with the change in protein/type of mutation:

TABLE 6

| Repeats | Mer | Gene | PC |
|---|---|---|---|
| 4 | NRGLKKKKQ [SEQ ID NO: 4] | ['TAF1B'] | ['p.K63Kfs*6'] |
| 4 | LNRGLKKKK [SEQ ID NO: 5] | ['TAF1B'] | ['p.K63Kfs*6'] |
| 4 | RGLKKKKQY [SEQ ID NO: 6] | ['TAF1B'] | ['p.K63Kfs*6'] |
| 3 | TTLKLILVM [SEQ ID NO: 7] | ['RFC3'] | ['p.K79Kfs*27'] |
| 3 | GFVKAMINA [SEQ ID NO: 8] | ['SLC9A9'] | ['p.H190N'] |
| 3 | KKLKLAPLQ [SEQ ID NO: 9] | ['RFC3'] | ['p.K79Kfs*27'] |
| 3 | LILVMLEIV [SEQ ID NO: 10] | ['RFC3'] | ['p.K79Kfs*27'] |
| 3 | SSGAVSTRV [SEQ ID NO: 11] | ['KRTAP1-1'] | ['p.I116V'] |
| 3 | VRWCRPDCR [SEQ ID NO: 12] | ['KRTAP1-1'] | ['p.I116V'] |
| 3 | TPSKKKLKL [SEQ ID NO: 13] | ['RFC3'] | ['p.K79Kfs*27'] |
| 3 | DIAVTPLKL [SEQ ID NO: 14] | ['KMT2C'] | ['p.R380L'] |
| 3 | MHQQQQQQM [SEQ ID NO: 15] | ['PAXIP1'] | ['p.Q548del'] |

TABLE 6-continued

| Repeats | Mer | Gene | PC |
|---|---|---|---|
| 3 | PLQVTTTLK [SEQ ID NO: 16] | ['RFC3'] | ['p.K79Kfs*27'] |
| 3 | TTPSKKKLK [SEQ ID NO: 17] | ['RFC3'] | ['p.K79Kfs*27'] |
| 3 | ILVMLEIVT [SEQ ID NO: 18] | ['RFC3'] | ['p.K79Kfs*27'] |
| 3 | VSTRVRWCR [SEQ ID NO: 19] | ['KRTAP1-1'] | ['p.I116V'] |
| 3 | LKLAPLQVT [SEQ ID NO: 20] | ['RFC3'] | ['p.K79Kfs*27'] |
| 3 | KAMINAGQL [SEQ ID NO: 21] | ['SLC9A9'] | ['p.H190N'] |
| 3 | SCLPSCNNR [SEQ ID NO: 22] | ['FAM72B'] | ['p.G99R'] |
| 3 | KLAPLQVTT [SEQ ID NO :23] | ['RFC3'] | ['p.K79Kfs*27'] |
| 3 | PSKKKLKLA [SEQ ID NO: 24] | ['RFC3'] | ['p.K79Kfs*27'] |
| 3 | NAGQLKNGD [SEQ ID NO: 25] | ['SLC9A9'] | ['p.H190N'] |
| 3 | HQQQQQQMQ [SEQ ID NO: 26] | ['PAXIP1'] | ['p.Q548del'] |
| 3 | LAGWQCPEC [SEQ ID NO: 27] | ['KMT2C'] | ['p.R380L'] |
| 3 | STRVRWCRP [SEQ ID NO: 28] | ['KRTAP1-1'] | ['p.I116V'] |

Similarly, Table 7 below shows exemplary results for common neoepitopes in ER+ breast cancer identified from a total of 43 samples. As above, the frequency is shown as Repeat, the neoepitope sequence as mer (9-mer).

TABLE 7

| Repeats | Mer | Gene |
|---|---|---|
| 11 | MKQMNDARH [SEQ ID NO: 29] | ['PIK3CA'] |
| 11 | RHGGWTTKM [SEQ ID NO: 30] | ['PIK3CA'] |
| 11 | ARHGGWTTK [SEQ ID NO: 31] | ['PIK3CA'] |
| 11 | QMNDARHGG [SEQ ID NO: 32] | ['PIK3CA'] |
| 11 | FMKQMNDAR [SEQ ID NO: 33] | ['PIK3CA'] |
| 11 | MNDARHGGW [SEQ ID NO: 34] | ['PIK3CA'] |
| 11 | KQMNDARHG [SEQ ID NO: 35] | ['PIK3CA'] |
| 11 | DARHGGWTT [SEQ ID NO: 36] | ['PIK3CA'] |
| 11 | NDARHGGWT [SEQ ID NO: 37] | ['PIK3CA'] |
| 4 | ASQIWNLNP [SEQ ID NO: 38] | ['USP8'] |
| 4 | SRLSASQIW [SEQ ID NO: 39] | ['USP8'] |
| 4 | SQIWNLNPV [SEQ ID NO: 40] | ['USP8'] |
| 4 | WNLNPVFGG [SEQ ID NO: 41] | ['USP8'] |
| 4 | RLSASQIWN [SEQ ID NO: 42] | ['USP8'] |

TABLE 7-continued

| Repeats | Mer | Gene |
|---|---|---|
| 4 | IWNLNPVFG [SEQ ID NO: 43] | ['USP8'] |
| 4 | SASQIWNLN [SEQ ID NO: 44] | ['USP8'] |
| 4 | QIWNLNPVF [SEQ ID NO: 45] | ['USP8'] |
| 4 | LSASQIWNL [SEQ ID NO: 46] | ['USP8'] |
| 3 | IQPVLWTTP [SEQ ID NO: 47] | ['GATA3'] |
| 3 | FETESASVT [SEQ ID NO: 48] | ['AK097289'] |
| 3 | LWTTPPLQH [SEQ ID NO: 49] | ['GATA3'] |
| 3 | ALQPLQPHA [SEQ ID NO: 50] | ['GATA3'] |
| 3 | SASVTQAGV [SEQ ID NO: 51] | ['AK097289'] |
| 3 | LQPLQPHAD [SEQ ID NO: 52] | ['GATA3'] |
| 3 | ASVTQAGVQ [SEQ ID NO: 53] | ['AK097289'] |

Table 8 below shows exemplary results for common neoepitopes in PR+ breast cancer identified from a total of 33 samples. As before, the frequency is shown as Repeat, the neoepitope sequence as mer (9-mer), and the affected gene is listed.

TABLE 8

| Repeats | Mer | Gene |
|---|---|---|
| 10 | QMNDARHGG [SEQ ID NO: 54] | ['PIK3CA'] |
| 10 | ARHGGWTTK [SEQ ID NO: 55] | ['PIK3CA'] |
| 10 | FMKQMNDAR [SEQ ID NO: 56] | ['PIK3CA'] |
| 10 | MKQMNDARH [SEQ ID NO: 57] | ['PIK3CA'] |
| 10 | DARHGGWTT [SEQ ID NO: 58] | ['PIK3CA'] |
| 10 | MNDARHGGW [SEQ ID NO: 59] | ['PIK3CA'] |
| 10 | KQMNDARHG [SEQ ID NO: 60] | ['PIK3CA'] |
| 10 | NDARHGGWT [SEQ ID NO: 61] | ['PIK3CA'] |
| 10 | RHGGWTTKM [SEQ ID NO: 62] | ['PIK3CA'] |
| 3 | FFEIESASV [SEQ ID NO: 63] | ['AK097289'] |
| 3 | EIESASVTQ [SEQ ID NO: 64] | ['AK097289'] |
| 3 | SFFFFEIES [SEQ ID NO: 65] | ['AK097289'] |
| 3 | TLCSFFFFE [SEQ ID NO: 66] | ['AK097289'] |
| 3 | FETESASVT [SEQ ID NO: 67] | ['AK097289'] |
| 3 | ASQIWNLNP [SEQ ID NO: 68] | ['USP8'] |
| 3 | QIWNLNPVF [SEQ ID NO: 69] | ['USP8'] |
| 3 | YLGSLQPLP [SEQ ID NO: 70] | ['AK097289'] |
| 3 | SASVTQAGV [SEQ ID NO: 71] | ['AK097289'] |
| 3 | TQAGVQWRY [SEQ ID NO: 72] | ['AK097289'] |
| 3 | SRLSASQIW [SEQ ID NO: 73] | ['USP8'] |
| 3 | RYLGSLQPL [SEQ ID NO: 74] | ['AK097289'] |

TABLE 8-continued

| Repeats | Mer | Gene |
|---|---|---|
| 3 | ASVTQAGVQ [SEQ ID NO: 75] | ['AK097289'] |
| 3 | QTLCSFFFF [SEQ ID NO: 76] | ['AK097289'] |
| 3 | SQIWNLNPV [SEQ ID NO: 77] | ['USP8'] |
| 3 | WNLNPVFGG [SEQ ID NO: 78] | ['USP8'] |

Likewise, Table 9 below shows exemplary results for common neoepitopes in HER2+ breast cancer identified from a total of 19 samples. As above, the frequency is shown as Repeat, the neoepitope sequence as mer (9-mer), and the affected gene is listed.

TABLE 9

| Repeat | Mer | Gene |
|---|---|---|
| 2 | LPASHPLFG [SEQ ID NO: 79] | ['LILRB1'] |
| 2 | ITNNFGSVA [SEQ ID NO: 80] | ['PANK3'] |
| 2 | LVTITNNFG [SEQ ID NO: 81] | ['PANK3'] |
| 2 | GPLPASHPL [SEQ ID NO: 82] | ['LILRB1'] |
| 2 | LVTSQESGQ [SEQ ID NO: 83] | ['FANCD2'] |
| 2 | VTITNNFGS [SEQ ID NO: 84] | ['PANK3'] |
| 2 | TLVTITNNF [SEQ ID NO: 85] | ['PANK3'] |
| 2 | TNNFGSVAR [SEQ ID NO: 86] | ['PANK3'] |
| 2 | LLPGPLPAS [SEQ ID NO: 87] | ['LILRB1'] |
| 2 | GGLVTSQES [SEQ ID NO: 88] | ['FANCD2'] |
| 2 | TKQEKDFLW [SEQ ID NO: 89] | ['PIK3CA'] |
| 2 | ATCSHYTQL [SEQ ID NO: 90] | ['CLEC18B'] |
| 2 | FAKDGGLVT [SEQ ID NO: 91] | ['FANCD2'] |
| 2 | KQEKDFLWS [SEQ ID NO: 92] | ['PIK3CA'] |
| 2 | DPLSEITKQ [SEQ ID NO: 93] | ['PIK3CA'] |
| 2 | ECARNATCS [SEQ ID NO: 94] | ['CLEC18B'] |
| 2 | PASHPLFGR [SEQ ID NO: 95] | ['LILRB1'] |
| 2 | FGSVARMCA [SEQ ID NO: 96] | ['PANK3'] |
| 2 | EITKQEKDF [SEQ ID NO: 97] | ['PIK3CA'] |
| 2 | ITKQEKDFL [SEQ ID NO: 98] | ['PIK3CA'] |
| 2 | LSEITKQEK [SEQ ID NO: 99] | ['PIK3CA'] |
| 2 | RNATCSHYT [SEQ ID NO: 100] | ['CLEC18B'] |
| 2 | SEITKQEKD [SEQ ID NO: 101] | ['PIK3CA'] |
| 2 | AKDGGLVTS [SEQ ID NO: 102] | ['FANCD2'] |
| 2 | LPGPLPASH [SEQ ID NO: 103] | ['LILRB1'] |

Therefore, it should be recognized that despite the fairly large number of individual neoepitopes in each cancer, several shared neoepitopes were nevertheless identified. Moreover, as can also be taken from the data in Tables 3 and 6-9, the neoepitopes affected the same gene, and in most cases even the same position. In addition, it should be noted that the above neoepitopes are not reflective of a change in sequence relative to a reference sequence from a healthy human, but are reflective of a change in sequence in the tumor of a patient relative to a healthy control sequence from the same patient.

Consequently, it should be appreciated that despite the apparent vast diversity of cancer neoepitopes, there are selected neoepitope sequences that are common among various cancer types as shown in Table 3 and that are common among different cancer subtypes as can be seen from Tables 3-6. Interestingly, some of the neoepitopes that were present in one subtype were also present in another subtype and may as such serve as a common marker for diagnosis and/or treatment.

Where common neoepitopes were not known or available, the inventors also used an approach similar to the methods discussed above to identify from whole genome sequencing data of tumor and matched normal patient samples a plurality of cancer neoepitopes. The same omics information was also used to predict the HLA-type, and after filtering for the expression levels and subtracting epitopes occurring in healthy tissue, the calculated neoepitopes were subjected to an in silico binding analysis to determine binding of the neoepitopes to the HLA. More particularly, 108 unique neoepitopes in a total of 108 neoepitopes were identified in an LA tumor with a total of 12 coding variants. The patient tumor was predicted to have HLA-A 24:02, HLA-B15:53, and HLA-DRB1 15:28. In silico HLA binding analysis (e.g., using netMHC) and there was a HLA super type match with HLA-B*15:01, with 4 amino acid difference from patient's predicted allele HLA-B*15:53, and no matches were found to HLA-A*24:02 as is shown in the exemplary data of Table 10 below. Strong binding is typically predicted for calculated values of <50 nM, and weak binding for calculated values of <500 nM.

TABLE 10

| Gene | Mer | Binding Affinity (nM) | HLA |
|---|---|---|---|
| OXER1 | LTAIALNCY [SEQ ID NO: 104] | 141 | HLA-B15:01 |
| OXER1 | IALNCYLKV [SEQ ID NO: 105] | 384 | HLA-B15:03 |
| UTP20 | QKKRKALEF [SEQ ID NO: 106] | 10 | HLA-B15:03 |
| MRPL55 | ICYREPRRM [SEQ ID NO: 107] | 460 | HLA-B15:03 |
| PDZD8 | VFLGEMVPF [SEQ ID NO: 108] | 170 | HLA-B15:03 |

As can be readily seen from the above, computational analysis of multiple omics data for tumor-matched normal data sets allows for identification of neoepitopes that may be common or shared between different cancers and even different cancer subtypes. Moreover, when taken together with computational analysis of HLA-binding, neoepitope targets can be identified that may serve as immunological targets using various affinity molecules. Consequently, it should be appreciated that neoepitopes as identified herein can be used for various compositions and methods suitable for immunotherapy, either directly as immunogenic peptides used for vaccination (e.g., in association with a carrier), or indirectly as targets for molecules that specifically bind to the identified neoepitopes. For example, antibodies may be raised against the neoepitopes and so prepared antibodies may be used as cancer and neoepitope-specific targeting moiety. Of course, it should be appreciated that the antibodies may be full length immunoglobulins, fragments thereof, or synthetic antibodies or scFvs, or may even be part of a chimeric molecule (e.g., chimeric T-cell receptor).

Therefore, the inventors also contemplate a method of directing an agent to a cancer cell in which the cancer cell is contacted with an antibody or fragment thereof that binds to a cancer neoepitope as presented herein. For example, the neoepitope may be located in AGGF1, and may be formed by a V202L mutation in the AGGF1 protein. Therefore, suitable cancer epitopes especially include those having a sequence of SEQ ID NO:1, SEQ ID NO:2, or SEQ ID NO:3. Most typically, cancer cells found with such neoepitopes include various cancer cells such as BRCA (breast cancer) cells, CESC (cervical squamous cell carcinoma) cells, HNSC (head and neck squamous cell carcinoma) cells, LIHC (liver hepatocellular carcinoma) cells, LUAD (lung adenocarcinoma) cells, LUSC (lung squamous cell carcinoma) cells, OV (ovarian cancer) cells, READ (renal adenocarcinoma) cells, STAD (stomach adenocarcinoma) cells, THCA (thyroid carcinoma) cells, or UCEC (uterine corpus endometrioid carcinoma) cells.

On the other hand, where the cancer cell is a breast cancer cell, suitable neoepitopes will have a sequence of any one of SEQ ID NO:4 to SEQ ID NO:103. For example, for triple negative breast cancer cells, contemplated neoepitopes have a sequence of any one of SEQ ID NO:4 to SEQ ID NO:28, and for ER positive breast cancer cells, the neoepitope have a sequence of any one of SEQ ID NO:29 to SEQ ID NO:53. On the other hand, where the cancer cells are PR positive breast cancer cells, the neoepitope has a sequence of any one of SEQ ID NO:54 to SEQ ID NO:78, and where the cancer cells are HER2 positive breast cancer cells, the neoepitope has a sequence of any one of SEQ ID NO:79 to SEQ ID NO:103. Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified, thus fulfilling the written description of all Markush groups used in the appended claims.

With respect to suitable antibodies or antibody fragments it should be noted that the antibodies or fragments thereof may be generated in numerous manners well known in the art. Therefore, it should be appreciated that the antibodies or fragments may be synthetic or obtained via immunization of a mammal using one or more of the identified neoepitopes. Consequently, contemplated antibodies or fragments thereof may comprises IgG antibodies, a Fab, a F(ab')$_2$, or a scFv. Viewed from a different perspective, the inventors contemplate an antibody or fragment thereof that binds to a cancer neoepitope having a sequence of any one of SEQ ID NO:4 to SEQ ID NO:103. Therefore, it should be appreciated that the inventors contemplate the use of an antibody or fragment thereof to direct a diagnostic or therapeutic agent to a cancer cell, wherein the antibody or fragment thereof binds to a cancer neoepitope having a sequence of any one of SEQ ID NO:4 to SEQ ID NO:103. Where generation of an antibody is not desired, it is also contemplated that antibody libraries can be searched for one or more antibodies that bind to the neoantigen.

Of course, it should also be appreciated that the antibody or fragment thereof may be coupled to a therapeutic agent, a radiologic agent, and/or an imaging agent. For example, contemplated therapeutic agents include various chemotherapeutic drugs to so deliver the chemotherapeutic drug directly to a cancer cell. On the other hand, a radiologic agent may be coupled to the antibody or fragment thereof to selectively destroy a cancer cell and suitable radiologic agents include all agents suitable for brachytherapy, and especially $^{125}$I, $^{103}$Pd, or $^{192}$Ir. Alternatively, boron-10 may be used where neutron capture therapy with low-energy thermal neutrons is desired. Likewise, imaging agents may be coupled to the antibody or fragment thereof, and especially preferred imaging agents include PET (e.g., $^{11}$C, $^{13}$N, $^{15}$O, and $^{18}$F) and SPECT labels (e.g., $^{123}$I, $^{99m}$Tc, $^{133}$Xe, $^{201}$Tl, and $^{18}$F). As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Where the neoepitopes are employed in immune cell targeting, it should be noted that the antibody or fragment thereof may also be coupled to a portion of a T-cell receptor or a cytotoxic T-cell or an NK cell. Most preferably, where the antibody or fragment thereof is used in a chimeric T-cell receptor of a cytotoxic T-cell, the antigen binding portion of the chimeric T-cell receptor may have a scFv as ectodomain where the scFv has binding affinity against one of the neoepitopes of SEA ID NO:4-SEQ ID NO:103. On the other hand, where the antibody or fragment thereof is used with an NK cell, especially preferred NK cells are NK-92 derivatives that are modified to have a reduced or abolished expression of at least one killer cell immunoglobulin-like receptor (KIR), which will render such cells constitutively activated (via lack of or reduced inhibition). For example, such NK cells may be obtained from NantKwest (see nantkwest.com) as aNK cells ('activated natural killer cells) and may then be further modified to express a membrane bound antibody or fragment thereof with binding affinity to any one of the neoepitopes of SEA ID NO:4-SEQ ID NO:103.

Alternatively, the NK cell may also be a NK-92 derivative that is modified to express the high-affinity Fcγ receptor (CD16), and it is especially contemplated that the antibodies contemplated herein may be bound to such modified NK cells. Such cells may be obtained from NantKwest as haNK cells ('high-affinity natural killer cells). Likewise, the NK cell may also be genetically engineered to express a chimeric T-cell receptor. In especially preferred aspects, the chimeric T-cell receptor will have an scFv portion or other ectodomain with binding specificity against any one of the neoepitopes of SEA ID NO:4-SEQ ID NO:103.

Depending on the particular composition, it should therefore be appreciated that the step of contacting the cancer cell may be performed in vitro, in a non-patient mammal, or in the patient. For example, where the antibody of fragment thereof is used in diagnosis, the step of contacting may include binding the antibody of fragment thereof to a tissue sample ex vivo. (e.g., on a microscope slide to a FFPE sample) On the other hand, where binding efficacy is tested in vitro, the antibody of fragment thereof may be added to a tissue culture of a patient tumor. In still other uses, the antibody of fragment thereof may be administered to a patient in need thereof to provide a therapeutic, radiologic, or diagnostic agent to the cancer cell in vivo.

In further contemplated examples, the above noted neoepitopes are also suitable as immunostimulatory peptides, which may be administered to a mammal (and especially a patient) in form of an immunostimulatory composition. For example, the inventors contemplate an immunologic composition comprising a carrier to which is coupled a peptide having a sequence of any one of SEQ ID NO:4 to SEQ ID NO:28, of any one of SEQ ID NO:29 to SEQ ID NO:53, of any one of SEQ ID NO:54 to SEQ ID NO:78, or of any one of SEQ ID NO:79 to SEQ ID NO:103, and wherein the composition is formulated as a vaccine. Of course, it should be appreciated that such immunostimulatory peptides may comprise additional peptide portions that may be identical or different. For example, contemplated immunostimulatory peptides may comprise multiple neoantigens that may be separated by spacers (preferably flexible linkers such as GS4 linkers, etc.), typically comprising between 2 and 10 neoantigens. Use of such immunostimulatory composition may be prophylactically to provide a preventive protective immunity to a patient, or therapeutically to elicit an immune response to the neoepitopes, which is expected to translate to a therapeutic immune response against the tumor having such neoepitopes. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

Moreover, it should be noted that the neoantigens presented herein may be further modified to improve binding affinity to a specific HLA-type, and particularly preferred positions for modification of the neoepitope sequence are at the termini Consequently, the length of a neoepitope may vary. However, generally preferred that the length is between 8 and 11 amino acids (e.g., 9 mers), particularly where they are intended for MHC-I presentation. For MHC-II presentation, the neoepitope sequences presented herein may be extended to an overall length of between about 15-25 amino acids. Thus, modified neoepitopes are also specifically contemplated that will have a sequence identity of less than 100% as compared any one of SEQ ID NO: 1-103. For example, identity may be between 90-100%, or between 85-95%, or between 80-90%, or between 70-80%, or even less.

In yet further examples, the neoepitopes may also be expressed in a host cell (and typically a patient cell) form a recombinant nucleic acid, and all recombinant nucleic acids for such purpose are deemed suitable for use herein. Therefore, suitable recombinant nucleic acids will include a promoter sequence that is operably coupled to a nucleic acid sequence that encodes a protein having a sequence of any one of SEQ ID NO:4 to SEQ ID NO:103. Of course, it should be appreciated that the recombinant nucleic acid may comprise more than one sequence that encodes a neoepitope presented herein, and suitable recombinant nucleic acids will include at least two, three, four, five, or more sequence portions that encode the same or different neoepitopes. For example, suitable recombinant nucleic acids include expression vectors, and especially bacterial and viral expression vectors. However, naked DNA or linear DNA is also contemplated, particularly where the recombinant nucleic acid is used as a DNA vaccine. Thus, it should also be noted that where neoepitopes are expressed form a recombinant nucleic acid, that neoepitope is expressed in and presented on cells other than tumor cells, which is also a reflection of the recombinant nature of the so modified cell. Viewed from another perspective, the neoepitope outside the context of a cancer cell is a purely man-made, albeit in vivo, construct that would otherwise not occur.

Where recombinant viruses are employed, it is contemplated that all known manners of making recombinant viruses are deemed suitable for use herein, however, especially preferred viruses are those already established in gene therapy, including adenoviruses, adeno-associated viruses, alphaviruses, herpes viruses, lentiviruses, etc. However, among other appropriate choices, adenoviruses are particularly preferred. Moreover, it is further generally preferred that the virus is a replication deficient and non-immunogenic virus, which is typically accomplished by targeted deletion of selected viral proteins (e.g., E1, E3 proteins). Such desirable properties may be further enhanced by deleting E2b gene function, and high titers of recombinant viruses can be achieved using genetically modified human 293 cells as has been recently reported (e.g., *J Virol.* 1998 February; 72(2): 926-933). Most typically, the desired nucleic acid sequences (for expression from virus infected cells) are under the control of appropriate regulatory elements well known in the art.

With respect to the 'payload' of the genetically modified (adeno)virus it is contemplated that expression of more than one neoepitope is preferred, for example two, three, four, five, and even more, which can be accomplished using multiple distinct modified viruses, or a virus having more than one neoepitope sequence (e.g., as concatemeric or chimeric sequence). While not limiting to the inventive subject matter, it is generally preferred that neoepitope sequences are configured as a tandem minigene (e.g., $aa_{12}$-neoepitope$_{12}$-$aa_{12}$), or as single transcriptional unit, which may or may not be translated to a chimeric protein. Thus, it should be appreciated that the epitopes can be presented as monomers, multimers, individually or concatemeric, or as hybrid sequences with N- and/or C-terminal peptides. Most typically, it is preferred that the nucleic acid sequence is back-translated using suitable codon usage to accommodate the virus and/or host codon preference. However, alternate codon usage or non-matched codon usage is also deemed appropriate.

Viruses may then be individually or in combination used as a therapeutic vaccine in a pharmaceutical composition, typically formulated as a sterile injectable composition with a virus titer of between $10^4$-$10^{11}$ virus particles per dosage unit. However, alternative formulations are also deemed suitable for use herein, and all known routes and modes of administration are contemplated herein. As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.).

Lastly, it should be noted that where the virus comprises a nucleic acid payload that encodes multiple neoepitopes, it is contemplated that multiple neoepitopes may at least additively or synergistically enhance the host immune response. Similarly, where multiple viruses are used with each virus having a different neoepitope, it is contemplated that multiple neoepitopes may at least additively or synergistically enhance the host immune response. Such additive or synergistic effect may be genuine to a specific tumor or stage, or specific to particular patient parameter (e.g., age, gender, previous treatment, etc.)

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Moreover, all methods described herein can be performed in any suitable order unless otherwise indicated herein or otherwise clearly contradicted by context.

It should be apparent to those skilled in the art that many more modifications besides those already described are possible without departing from the inventive concepts herein. The inventive subject matter, therefore, is not to be restricted except in the scope of the appended claims.

Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc. Lastly, The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The invention claimed is:

1. An immunologic composition comprising:
   a carrier to which is coupled a peptide comprising the sequence of SEQ ID NO:1, SEQ ID NO:2, and/or SEQ ID NO:3; and
   wherein the composition is formulated as a vaccine.

2. The immunologic composition of claim 1 wherein the peptide comprises the sequence of SEQ ID NO:1.

3. The immunologic composition of claim 1 wherein the peptide comprises the sequence of SEQ ID NO:2.

4. The immunologic composition of claim 1 wherein the peptide comprises the sequence of SEQ ID NO:3.

5. The immunologic composition of claim 1 wherein the peptide is further coupled to at least one additional cancer neoepitope peptide.

6. The immunologic composition of claim 1 wherein the additional peptide has the sequence of any one of SEQ ID NO:4 to SEQ ID NO:28, of any one of SEQ ID NO:29 to SEQ ID NO:53, of any one of SEQ ID NO:54 to SEQ ID NO:78, or of any one of SEQ ID NO:79 to SEQ ID NO:103.

7. A method comprising administering the immunologic composition of claim 1 to a patient in need thereof to treat BRCA (breast cancer), CESC (cervical squamous cell carcinoma), HNSC (head and neck squamous cell carcinoma), LIHC (liver hepatocellular carcinoma), LUAD (lung adenocarcinoma), LUSC (lung squamous cell carcinoma), OV (ovarian cancer), READ (renal adenocarcinoma), STAD (stomach adenocarcinoma), THCA (thyroid carcinoma), or UCEC (uterine corpus endometrioid carcinoma).

8. The method of claim 7 wherein the vaccine is administered to a mammal having an HLA type selected from the group consisting of HLA-A*29:02 and HLA-A*30:02.

9. The method of claim 7 wherein the vaccine is administered to a mammal having an HLA type selected from the group consisting of HLA-B*15:01, HLA-B*15:02, HLA-B*15:03, HLA-B*15:17, HLA-B*35:01, HLA-B*40:02, HLA-B*44:02, and HLA-B*45:01.

* * * * *

SEQUENCE LISTING

```
<160> NUMBER OF SEQ ID NOS: 108

<210> SEQ ID NO 1
<211> LENGTH: 9
<212> TYPE: PRT
<213> ORGANISM: Homo sapiens

<400> SEQUENCE: 1

Ala Glu Ala Ala Leu Ser Gln Thr Gly
1               5

<210> SEQ ID NO 2
<211> LENGTH: 9
<212> TYPE: PRT
<213> ORGANISM: Homo sapiens

<400> SEQUENCE: 2

Ala Leu Ser Gln Thr Gly Phe Ser Tyr
1               5

<210> SEQ ID NO 3
<211> LENGTH: 9
<212> TYPE: PRT
<213> ORGANISM: Homo sapiens

<400> SEQUENCE: 3

Glu Ala Ala Leu Ser Gln Thr Gly Phe
1               5

<210> SEQ ID NO 4
<211> LENGTH: 9
<212> TYPE: PRT
<213> ORGANISM: Homo sapiens

<400> SEQUENCE: 4

Asn Arg Gly Leu Lys Lys Lys Lys Gln
1               5

<210> SEQ ID NO 5
<211> LENGTH: 9
<212> TYPE: PRT
<213> ORGANISM: Homo sapiens

<400> SEQUENCE: 5
```

Leu Asn Arg Gly Leu Lys Lys Lys Lys
1               5

<210> SEQ ID NO 6
<211> LENGTH: 9
<212> TYPE: PRT
<213> ORGANISM: Homo sapiens

<400> SEQUENCE: 6

Arg Gly Leu Lys Lys Lys Lys Gln Tyr
1               5

<210> SEQ ID NO 7
<211> LENGTH: 9
<212> TYPE: PRT
<213> ORGANISM: Homo sapiens

<400> SEQUENCE: 7

Thr Thr Leu Lys Leu Ile Leu Val Met
1               5

<210> SEQ ID NO 8
<211> LENGTH: 9
<212> TYPE: PRT
<213> ORGANISM: Homo sapiens

<400> SEQUENCE: 8

Gly Phe Val Lys Ala Met Ile Asn Ala
1               5

<210> SEQ ID NO 9
<211> LENGTH: 9
<212> TYPE: PRT
<213> ORGANISM: Homo sapiens

<400> SEQUENCE: 9

Lys Lys Leu Lys Leu Ala Pro Leu Gln
1               5

<210> SEQ ID NO 10
<211> LENGTH: 9
<212> TYPE: PRT
<213> ORGANISM: Homo sapiens

<400> SEQUENCE: 10

Leu Ile Leu Val Met Leu Glu Ile Val
1               5

<210> SEQ ID NO 11
<211> LENGTH: 9
<212> TYPE: PRT
<213> ORGANISM: Homo sapiens

<400> SEQUENCE: 11

Ser Ser Gly Ala Val Ser Thr Arg Val
1               5

<210> SEQ ID NO 12
<211> LENGTH: 9
<212> TYPE: PRT
<213> ORGANISM: Homo sapiens

<400> SEQUENCE: 12

Val Arg Trp Cys Arg Pro Asp Cys Arg

<210> SEQ ID NO 13
<211> LENGTH: 9
<212> TYPE: PRT
<213> ORGANISM: Homo sapiens

<400> SEQUENCE: 13

Thr Pro Ser Lys Lys Lys Leu Lys Leu
1               5

<210> SEQ ID NO 14
<211> LENGTH: 9
<212> TYPE: PRT
<213> ORGANISM: Homo sapiens

<400> SEQUENCE: 14

Asp Ile Ala Val Thr Pro Leu Lys Leu
1               5

<210> SEQ ID NO 15
<211> LENGTH: 9
<212> TYPE: PRT
<213> ORGANISM: Homo sapiens

<400> SEQUENCE: 15

Met His Gln Gln Gln Gln Gln Gln Met
1               5

<210> SEQ ID NO 16
<211> LENGTH: 9
<212> TYPE: PRT
<213> ORGANISM: Homo sapiens

<400> SEQUENCE: 16

Pro Leu Gln Val Thr Thr Thr Leu Lys
1               5

<210> SEQ ID NO 17
<211> LENGTH: 9
<212> TYPE: PRT
<213> ORGANISM: Homo sapiens

<400> SEQUENCE: 17

Thr Thr Pro Ser Lys Lys Lys Leu Lys
1               5

<210> SEQ ID NO 18
<211> LENGTH: 9
<212> TYPE: PRT
<213> ORGANISM: Homo sapiens

<400> SEQUENCE: 18

Ile Leu Val Met Leu Glu Ile Val Thr
1               5

<210> SEQ ID NO 19
<211> LENGTH: 9
<212> TYPE: PRT
<213> ORGANISM: Homo sapiens

<400> SEQUENCE: 19

Val Ser Thr Arg Val Arg Trp Cys Arg
1               5

<210> SEQ ID NO 20
<211> LENGTH: 9
<212> TYPE: PRT
<213> ORGANISM: Homo sapiens

<400> SEQUENCE: 20

Leu Lys Leu Ala Pro Leu Gln Val Thr
1               5

<210> SEQ ID NO 21
<211> LENGTH: 9
<212> TYPE: PRT
<213> ORGANISM: Homo sapiens

<400> SEQUENCE: 21

Lys Ala Met Ile Asn Ala Gly Gln Leu
1               5

<210> SEQ ID NO 22
<211> LENGTH: 9
<212> TYPE: PRT
<213> ORGANISM: Homo sapiens

<400> SEQUENCE: 22

Ser Cys Leu Pro Ser Cys Asn Asn Arg
1               5

<210> SEQ ID NO 23
<211> LENGTH: 9
<212> TYPE: PRT
<213> ORGANISM: Homo sapiens

<400> SEQUENCE: 23

Lys Leu Ala Pro Leu Gln Val Thr Thr
1               5

<210> SEQ ID NO 24
<211> LENGTH: 9
<212> TYPE: PRT
<213> ORGANISM: Homo sapiens

<400> SEQUENCE: 24

Pro Ser Lys Lys Lys Leu Lys Leu Ala
1               5

<210> SEQ ID NO 25
<211> LENGTH: 9
<212> TYPE: PRT
<213> ORGANISM: Homo sapiens

<400> SEQUENCE: 25

Asn Ala Gly Gln Leu Lys Asn Gly Asp
1               5

<210> SEQ ID NO 26
<211> LENGTH: 9
<212> TYPE: PRT
<213> ORGANISM: Homo sapiens

<400> SEQUENCE: 26

His Gln Gln Gln Gln Gln Met Gln
1               5

<210> SEQ ID NO 27

```
<211> LENGTH: 9
<212> TYPE: PRT
<213> ORGANISM: Homo sapiens

<400> SEQUENCE: 27

Leu Ala Gly Trp Gln Cys Pro Glu Cys
1               5

<210> SEQ ID NO 28
<211> LENGTH: 9
<212> TYPE: PRT
<213> ORGANISM: Homo sapiens

<400> SEQUENCE: 28

Ser Thr Arg Val Arg Trp Cys Arg Pro
1               5

<210> SEQ ID NO 29
<211> LENGTH: 9
<212> TYPE: PRT
<213> ORGANISM: Homo sapiens

<400> SEQUENCE: 29

Met Lys Gln Met Asn Asp Ala Arg His
1               5

<210> SEQ ID NO 30
<211> LENGTH: 9
<212> TYPE: PRT
<213> ORGANISM: Homo sapiens

<400> SEQUENCE: 30

Arg His Gly Gly Trp Thr Thr Lys Met
1               5

<210> SEQ ID NO 31
<211> LENGTH: 9
<212> TYPE: PRT
<213> ORGANISM: Homo sapiens

<400> SEQUENCE: 31

Ala Arg His Gly Gly Trp Thr Thr Lys
1               5

<210> SEQ ID NO 32
<211> LENGTH: 9
<212> TYPE: PRT
<213> ORGANISM: Homo sapiens

<400> SEQUENCE: 32

Gln Met Asn Asp Ala Arg His Gly Gly
1               5

<210> SEQ ID NO 33
<211> LENGTH: 9
<212> TYPE: PRT
<213> ORGANISM: Homo sapiens

<400> SEQUENCE: 33

Phe Met Lys Gln Met Asn Asp Ala Arg
1               5

<210> SEQ ID NO 34
<211> LENGTH: 9
<212> TYPE: PRT
```

```
<213> ORGANISM: Homo sapiens

<400> SEQUENCE: 34

Met Asn Asp Ala Arg His Gly Gly Trp
1               5

<210> SEQ ID NO 35
<211> LENGTH: 9
<212> TYPE: PRT
<213> ORGANISM: Homo sapiens

<400> SEQUENCE: 35

Lys Gln Met Asn Asp Ala Arg His Gly
1               5

<210> SEQ ID NO 36
<211> LENGTH: 9
<212> TYPE: PRT
<213> ORGANISM: Homo sapiens

<400> SEQUENCE: 36

Asp Ala Arg His Gly Gly Trp Thr Thr
1               5

<210> SEQ ID NO 37
<211> LENGTH: 9
<212> TYPE: PRT
<213> ORGANISM: Homo sapiens

<400> SEQUENCE: 37

Asn Asp Ala Arg His Gly Gly Trp Thr
1               5

<210> SEQ ID NO 38
<211> LENGTH: 9
<212> TYPE: PRT
<213> ORGANISM: Homo sapiens

<400> SEQUENCE: 38

Ala Ser Gln Ile Trp Asn Leu Asn Pro
1               5

<210> SEQ ID NO 39
<211> LENGTH: 9
<212> TYPE: PRT
<213> ORGANISM: Homo sapiens

<400> SEQUENCE: 39

Ser Arg Leu Ser Ala Ser Gln Ile Trp
1               5

<210> SEQ ID NO 40
<211> LENGTH: 9
<212> TYPE: PRT
<213> ORGANISM: Homo sapiens

<400> SEQUENCE: 40

Ser Gln Ile Trp Asn Leu Asn Pro Val
1               5

<210> SEQ ID NO 41
<211> LENGTH: 9
<212> TYPE: PRT
<213> ORGANISM: Homo sapiens
```

```
<400> SEQUENCE: 41

Trp Asn Leu Asn Pro Val Phe Gly Gly
1               5

<210> SEQ ID NO 42
<211> LENGTH: 9
<212> TYPE: PRT
<213> ORGANISM: Homo sapiens

<400> SEQUENCE: 42

Arg Leu Ser Ala Ser Gln Ile Trp Asn
1               5

<210> SEQ ID NO 43
<211> LENGTH: 9
<212> TYPE: PRT
<213> ORGANISM: Homo sapiens

<400> SEQUENCE: 43

Ile Trp Asn Leu Asn Pro Val Phe Gly
1               5

<210> SEQ ID NO 44
<211> LENGTH: 9
<212> TYPE: PRT
<213> ORGANISM: Homo sapiens

<400> SEQUENCE: 44

Ser Ala Ser Gln Ile Trp Asn Leu Asn
1               5

<210> SEQ ID NO 45
<211> LENGTH: 9
<212> TYPE: PRT
<213> ORGANISM: Homo sapiens

<400> SEQUENCE: 45

Gln Ile Trp Asn Leu Asn Pro Val Phe
1               5

<210> SEQ ID NO 46
<211> LENGTH: 9
<212> TYPE: PRT
<213> ORGANISM: Homo sapiens

<400> SEQUENCE: 46

Leu Ser Ala Ser Gln Ile Trp Asn Leu
1               5

<210> SEQ ID NO 47
<211> LENGTH: 9
<212> TYPE: PRT
<213> ORGANISM: Homo sapiens

<400> SEQUENCE: 47

Ile Gln Pro Val Leu Trp Thr Thr Pro
1               5

<210> SEQ ID NO 48
<211> LENGTH: 9
<212> TYPE: PRT
<213> ORGANISM: Homo sapiens

<400> SEQUENCE: 48
```

Phe Glu Thr Glu Ser Ala Ser Val Thr
1               5

<210> SEQ ID NO 49
<211> LENGTH: 9
<212> TYPE: PRT
<213> ORGANISM: Homo sapiens

<400> SEQUENCE: 49

Leu Trp Thr Thr Pro Pro Leu Gln His
1               5

<210> SEQ ID NO 50
<211> LENGTH: 9
<212> TYPE: PRT
<213> ORGANISM: Homo sapiens

<400> SEQUENCE: 50

Ala Leu Gln Pro Leu Gln Pro His Ala
1               5

<210> SEQ ID NO 51
<211> LENGTH: 9
<212> TYPE: PRT
<213> ORGANISM: Homo sapiens

<400> SEQUENCE: 51

Ser Ala Ser Val Thr Gln Ala Gly Val
1               5

<210> SEQ ID NO 52
<211> LENGTH: 9
<212> TYPE: PRT
<213> ORGANISM: Homo sapiens

<400> SEQUENCE: 52

Leu Gln Pro Leu Gln Pro His Ala Asp
1               5

<210> SEQ ID NO 53
<211> LENGTH: 9
<212> TYPE: PRT
<213> ORGANISM: Homo sapiens

<400> SEQUENCE: 53

Ala Ser Val Thr Gln Ala Gly Val Gln
1               5

<210> SEQ ID NO 54
<211> LENGTH: 9
<212> TYPE: PRT
<213> ORGANISM: Homo sapiens

<400> SEQUENCE: 54

Gln Met Asn Asp Ala Arg His Gly Gly
1               5

<210> SEQ ID NO 55
<211> LENGTH: 9
<212> TYPE: PRT
<213> ORGANISM: Homo sapiens

<400> SEQUENCE: 55

Ala Arg His Gly Gly Trp Thr Thr Lys
1               5

<210> SEQ ID NO 56
<211> LENGTH: 9
<212> TYPE: PRT
<213> ORGANISM: Homo sapiens

<400> SEQUENCE: 56

Phe Met Lys Gln Met Asn Asp Ala Arg
1               5

<210> SEQ ID NO 57
<211> LENGTH: 9
<212> TYPE: PRT
<213> ORGANISM: Homo sapiens

<400> SEQUENCE: 57

Met Lys Gln Met Asn Asp Ala Arg His
1               5

<210> SEQ ID NO 58
<211> LENGTH: 9
<212> TYPE: PRT
<213> ORGANISM: Homo sapiens

<400> SEQUENCE: 58

Asp Ala Arg His Gly Gly Trp Thr Thr
1               5

<210> SEQ ID NO 59
<211> LENGTH: 9
<212> TYPE: PRT
<213> ORGANISM: Homo sapiens

<400> SEQUENCE: 59

Met Asn Asp Ala Arg His Gly Gly Trp
1               5

<210> SEQ ID NO 60
<211> LENGTH: 9
<212> TYPE: PRT
<213> ORGANISM: Homo sapiens

<400> SEQUENCE: 60

Lys Gln Met Asn Asp Ala Arg His Gly
1               5

<210> SEQ ID NO 61
<211> LENGTH: 9
<212> TYPE: PRT
<213> ORGANISM: Homo sapiens

<400> SEQUENCE: 61

Asn Asp Ala Arg His Gly Gly Trp Thr
1               5

<210> SEQ ID NO 62
<211> LENGTH: 9
<212> TYPE: PRT
<213> ORGANISM: Homo sapiens

<400> SEQUENCE: 62

Arg His Gly Gly Trp Thr Thr Lys Met
1               5

<210> SEQ ID NO 63
<211> LENGTH: 9
<212> TYPE: PRT
<213> ORGANISM: Homo sapiens

<400> SEQUENCE: 63

Phe Phe Glu Thr Glu Ser Ala Ser Val
1               5

<210> SEQ ID NO 64
<211> LENGTH: 9
<212> TYPE: PRT
<213> ORGANISM: Homo sapiens

<400> SEQUENCE: 64

Glu Thr Glu Ser Ala Ser Val Thr Gln
1               5

<210> SEQ ID NO 65
<211> LENGTH: 9
<212> TYPE: PRT
<213> ORGANISM: Homo sapiens

<400> SEQUENCE: 65

Ser Phe Phe Phe Phe Glu Thr Glu Ser
1               5

<210> SEQ ID NO 66
<211> LENGTH: 9
<212> TYPE: PRT
<213> ORGANISM: Homo sapiens

<400> SEQUENCE: 66

Thr Leu Cys Ser Phe Phe Phe Phe Glu
1               5

<210> SEQ ID NO 67
<211> LENGTH: 9
<212> TYPE: PRT
<213> ORGANISM: Homo sapiens

<400> SEQUENCE: 67

Phe Glu Thr Glu Ser Ala Ser Val Thr
1               5

<210> SEQ ID NO 68
<211> LENGTH: 9
<212> TYPE: PRT
<213> ORGANISM: Homo sapiens

<400> SEQUENCE: 68

Ala Ser Gln Ile Trp Asn Leu Asn Pro
1               5

<210> SEQ ID NO 69
<211> LENGTH: 9
<212> TYPE: PRT
<213> ORGANISM: Homo sapiens

<400> SEQUENCE: 69

Gln Ile Trp Asn Leu Asn Pro Val Phe
1               5

<210> SEQ ID NO 70
<211> LENGTH: 9

```
<212> TYPE: PRT
<213> ORGANISM: Homo sapiens

<400> SEQUENCE: 70

Tyr Leu Gly Ser Leu Gln Pro Leu Pro
1               5

<210> SEQ ID NO 71
<211> LENGTH: 9
<212> TYPE: PRT
<213> ORGANISM: Homo sapiens

<400> SEQUENCE: 71

Ser Ala Ser Val Thr Gln Ala Gly Val
1               5

<210> SEQ ID NO 72
<211> LENGTH: 9
<212> TYPE: PRT
<213> ORGANISM: Homo sapiens

<400> SEQUENCE: 72

Thr Gln Ala Gly Val Gln Trp Arg Tyr
1               5

<210> SEQ ID NO 73
<211> LENGTH: 9
<212> TYPE: PRT
<213> ORGANISM: Homo sapiens

<400> SEQUENCE: 73

Ser Arg Leu Ser Ala Ser Gln Ile Trp
1               5

<210> SEQ ID NO 74
<211> LENGTH: 9
<212> TYPE: PRT
<213> ORGANISM: Homo sapiens

<400> SEQUENCE: 74

Arg Tyr Leu Gly Ser Leu Gln Pro Leu
1               5

<210> SEQ ID NO 75
<211> LENGTH: 9
<212> TYPE: PRT
<213> ORGANISM: Homo sapiens

<400> SEQUENCE: 75

Ala Ser Val Thr Gln Ala Gly Val Gln
1               5

<210> SEQ ID NO 76
<211> LENGTH: 9
<212> TYPE: PRT
<213> ORGANISM: Homo sapiens

<400> SEQUENCE: 76

Gln Thr Leu Cys Ser Phe Phe Phe Phe
1               5

<210> SEQ ID NO 77
<211> LENGTH: 9
<212> TYPE: PRT
<213> ORGANISM: Homo sapiens
```

<400> SEQUENCE: 77

Ser Gln Ile Trp Asn Leu Asn Pro Val
1               5

<210> SEQ ID NO 78
<211> LENGTH: 9
<212> TYPE: PRT
<213> ORGANISM: Homo sapiens

<400> SEQUENCE: 78

Trp Asn Leu Asn Pro Val Phe Gly Gly
1               5

<210> SEQ ID NO 79
<211> LENGTH: 9
<212> TYPE: PRT
<213> ORGANISM: Homo sapiens

<400> SEQUENCE: 79

Leu Pro Ala Ser His Pro Leu Phe Gly
1               5

<210> SEQ ID NO 80
<211> LENGTH: 9
<212> TYPE: PRT
<213> ORGANISM: Homo sapiens

<400> SEQUENCE: 80

Ile Thr Asn Asn Phe Gly Ser Val Ala
1               5

<210> SEQ ID NO 81
<211> LENGTH: 9
<212> TYPE: PRT
<213> ORGANISM: Homo sapiens

<400> SEQUENCE: 81

Leu Val Thr Ile Thr Asn Asn Phe Gly
1               5

<210> SEQ ID NO 82
<211> LENGTH: 9
<212> TYPE: PRT
<213> ORGANISM: Homo sapiens

<400> SEQUENCE: 82

Gly Pro Leu Pro Ala Ser His Pro Leu
1               5

<210> SEQ ID NO 83
<211> LENGTH: 9
<212> TYPE: PRT
<213> ORGANISM: Homo sapiens

<400> SEQUENCE: 83

Leu Val Thr Ser Gln Glu Ser Gly Gln
1               5

<210> SEQ ID NO 84
<211> LENGTH: 9
<212> TYPE: PRT
<213> ORGANISM: Homo sapiens

<400> SEQUENCE: 84

```
Val Thr Ile Thr Asn Asn Phe Gly Ser
1               5
```

```
<210> SEQ ID NO 85
<211> LENGTH: 9
<212> TYPE: PRT
<213> ORGANISM: Homo sapiens

<400> SEQUENCE: 85
```

```
Thr Leu Val Thr Ile Thr Asn Asn Phe
1               5
```

```
<210> SEQ ID NO 86
<211> LENGTH: 9
<212> TYPE: PRT
<213> ORGANISM: Homo sapiens

<400> SEQUENCE: 86
```

```
Thr Asn Asn Phe Gly Ser Val Ala Arg
1               5
```

```
<210> SEQ ID NO 87
<211> LENGTH: 9
<212> TYPE: PRT
<213> ORGANISM: Homo sapiens

<400> SEQUENCE: 87
```

```
Leu Leu Pro Gly Pro Leu Pro Ala Ser
1               5
```

```
<210> SEQ ID NO 88
<211> LENGTH: 9
<212> TYPE: PRT
<213> ORGANISM: Homo sapiens

<400> SEQUENCE: 88
```

```
Gly Gly Leu Val Thr Ser Gln Glu Ser
1               5
```

```
<210> SEQ ID NO 89
<211> LENGTH: 9
<212> TYPE: PRT
<213> ORGANISM: Homo sapiens

<400> SEQUENCE: 89
```

```
Thr Lys Gln Glu Lys Asp Phe Leu Trp
1               5
```

```
<210> SEQ ID NO 90
<211> LENGTH: 9
<212> TYPE: PRT
<213> ORGANISM: Homo sapiens

<400> SEQUENCE: 90
```

```
Ala Thr Cys Ser His Tyr Thr Gln Leu
1               5
```

```
<210> SEQ ID NO 91
<211> LENGTH: 9
<212> TYPE: PRT
<213> ORGANISM: Homo sapiens

<400> SEQUENCE: 91
```

```
Phe Ala Lys Asp Gly Gly Leu Val Thr
```

```
1               5
```

<210> SEQ ID NO 92
<211> LENGTH: 9
<212> TYPE: PRT
<213> ORGANISM: Homo sapiens

<400> SEQUENCE: 92

```
Lys Gln Glu Lys Asp Phe Leu Trp Ser
1               5
```

<210> SEQ ID NO 93
<211> LENGTH: 9
<212> TYPE: PRT
<213> ORGANISM: Homo sapiens

<400> SEQUENCE: 93

```
Asp Pro Leu Ser Glu Ile Thr Lys Gln
1               5
```

<210> SEQ ID NO 94
<211> LENGTH: 9
<212> TYPE: PRT
<213> ORGANISM: Homo sapiens

<400> SEQUENCE: 94

```
Glu Cys Ala Arg Asn Ala Thr Cys Ser
1               5
```

<210> SEQ ID NO 95
<211> LENGTH: 9
<212> TYPE: PRT
<213> ORGANISM: Homo sapiens

<400> SEQUENCE: 95

```
Pro Ala Ser His Pro Leu Phe Gly Arg
1               5
```

<210> SEQ ID NO 96
<211> LENGTH: 9
<212> TYPE: PRT
<213> ORGANISM: Homo sapiens

<400> SEQUENCE: 96

```
Phe Gly Ser Val Ala Arg Met Cys Ala
1               5
```

<210> SEQ ID NO 97
<211> LENGTH: 9
<212> TYPE: PRT
<213> ORGANISM: Homo sapiens

<400> SEQUENCE: 97

```
Glu Ile Thr Lys Gln Glu Lys Asp Phe
1               5
```

<210> SEQ ID NO 98
<211> LENGTH: 9
<212> TYPE: PRT
<213> ORGANISM: Homo sapiens

<400> SEQUENCE: 98

```
Ile Thr Lys Gln Glu Lys Asp Phe Leu
1               5
```

```
<210> SEQ ID NO 99
<211> LENGTH: 9
<212> TYPE: PRT
<213> ORGANISM: Homo sapiens

<400> SEQUENCE: 99

Leu Ser Glu Ile Thr Lys Gln Glu Lys
1               5

<210> SEQ ID NO 100
<211> LENGTH: 9
<212> TYPE: PRT
<213> ORGANISM: Homo sapiens

<400> SEQUENCE: 100

Arg Asn Ala Thr Cys Ser His Tyr Thr
1               5

<210> SEQ ID NO 101
<211> LENGTH: 9
<212> TYPE: PRT
<213> ORGANISM: Homo sapiens

<400> SEQUENCE: 101

Ser Glu Ile Thr Lys Gln Glu Lys Asp
1               5

<210> SEQ ID NO 102
<211> LENGTH: 9
<212> TYPE: PRT
<213> ORGANISM: Homo sapiens

<400> SEQUENCE: 102

Ala Lys Asp Gly Gly Leu Val Thr Ser
1               5

<210> SEQ ID NO 103
<211> LENGTH: 9
<212> TYPE: PRT
<213> ORGANISM: Homo sapiens

<400> SEQUENCE: 103

Leu Pro Gly Pro Leu Pro Ala Ser His
1               5

<210> SEQ ID NO 104
<211> LENGTH: 9
<212> TYPE: PRT
<213> ORGANISM: Homo sapiens

<400> SEQUENCE: 104

Leu Thr Ala Ile Ala Leu Asn Cys Tyr
1               5

<210> SEQ ID NO 105
<211> LENGTH: 9
<212> TYPE: PRT
<213> ORGANISM: Homo sapiens

<400> SEQUENCE: 105

Ile Ala Leu Asn Cys Tyr Leu Lys Val
1               5

<210> SEQ ID NO 106
```

```
<211> LENGTH: 9
<212> TYPE: PRT
<213> ORGANISM: Homo sapiens

<400> SEQUENCE: 106

Gln Lys Lys Arg Lys Ala Leu Glu Phe
1               5

<210> SEQ ID NO 107
<211> LENGTH: 9
<212> TYPE: PRT
<213> ORGANISM: Homo sapiens

<400> SEQUENCE: 107

Ile Cys Tyr Arg Glu Pro Arg Arg Met
1               5

<210> SEQ ID NO 108
<211> LENGTH: 9
<212> TYPE: PRT
<213> ORGANISM: Homo sapiens

<400> SEQUENCE: 108

Val Phe Leu Gly Glu Met Val Pro Phe
1               5
```